United States Patent [19]

Davis et al.

[11] 4,421,408
[45] Dec. 20, 1983

[54] HALOGEN MASS FLOW RATE DETECTION SYSTEM

[75] Inventors: Steven J. Davis; Leonard Hanko, both of Albuquerque, N. Mex.

[73] Assignee: The United States of America as represented by the Secretary of the Air Force, Washington, D.C.

[21] Appl. No.: 237,021

[22] Filed: Feb. 23, 1981

[51] Int. Cl.$^3$ .................... G01N 1/22; G01N 21/85
[52] U.S. Cl. .................................. 356/246; 356/410
[58] Field of Search ..................... 356/246, 409, 410

[56] References Cited

U.S. PATENT DOCUMENTS

| | | | |
|---|---|---|---|
| 3,448,406 | 6/1969 | McClure | 331/94.5 |
| 3,549,262 | 12/1970 | Hozumi | 356/410 |
| 3,723,008 | 3/1973 | Fukuda et al. | 356/88 |
| 3,802,777 | 4/1974 | Regaier et al. | 356/75 |

Primary Examiner—Bruce Y. Arnold

Attorney, Agent, or Firm—Donald J. Singer; Jacob N. Erlich

[57] ABSTRACT

A halogen mass flow rate detection system having an absorption cell through which a halogen entrained inert gas can be passed. An electromagnetic beam of preselected wavelength in the bound-continuum absorption region is passed through the cell while the halogen entrained inert gas is passed therethrough and also while only an inert gas is passed through the cell. By measuring the intensity of the beam passing through the absorption cell, molecular absorption can be utilized for determining the concentration and, therefore, the mass flow rate of the halogen passing through the absorption cell. By incorporating the halogen mass flow rate detection system in an iodine/oxygen chemical laser, for example, the mass flow rate of the iodine into the resonant cavity of the laser can be simply, accurately and reliably ascertained.

10 Claims, 3 Drawing Figures

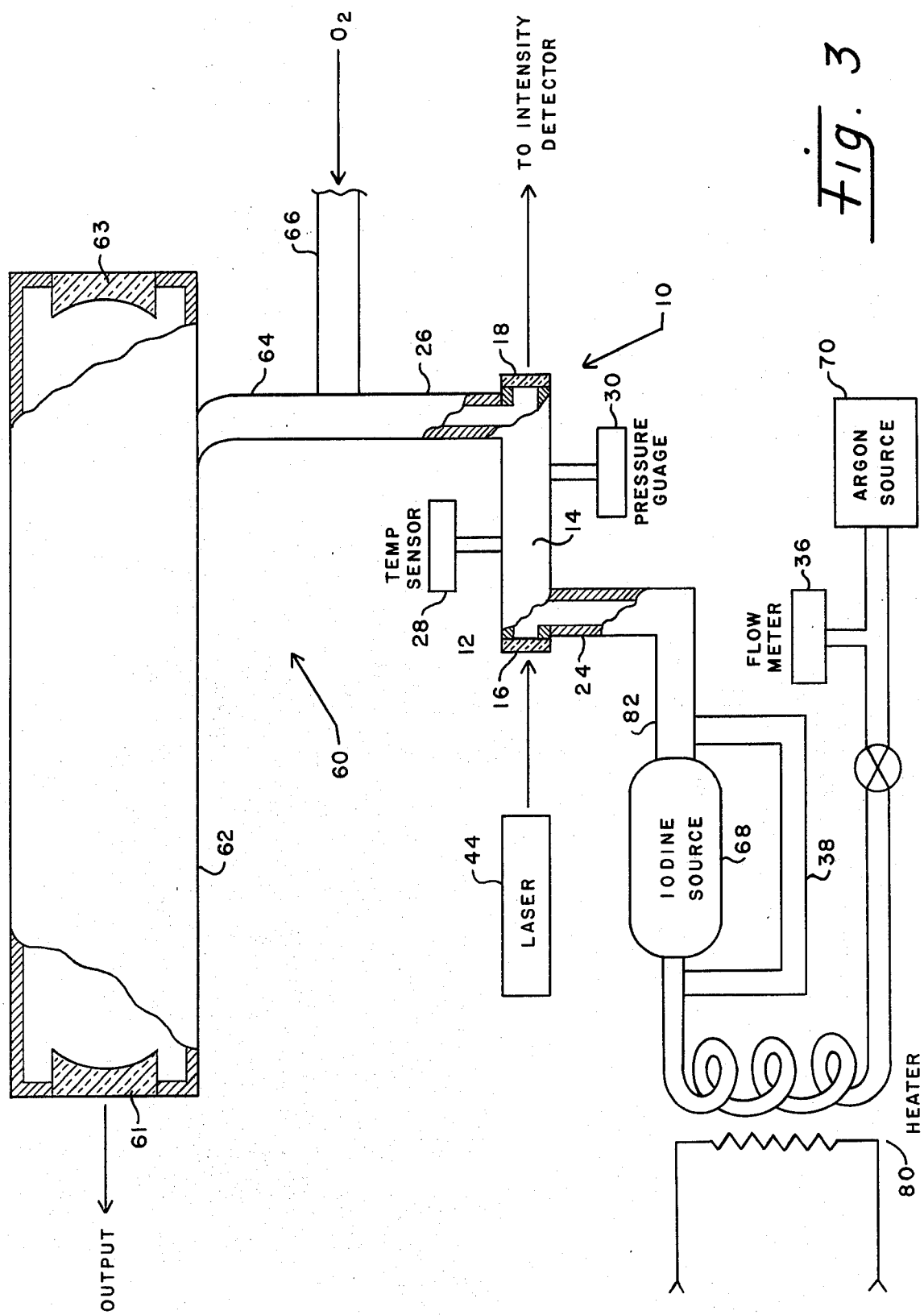

HALOGEN MASS FLOW RATE DETECTION SYSTEM

STATEMENT OF GOVERNMENT INTEREST

The invention described herein may be manufactured and used by or for the Government for governmental purposes without the payment of any royalty thereon.

BACKGROUND OF THE INVENTION

This invention relates generally to flow rate detection systems, and, more particularly to a halogen mass flow rate detection system which can be readily incorporated within a chemical laser.

Recent studies on chemical laser systems, and in particular oxygen/iodine chemical lasers have indicated a need for an accurate, diagnostic system for determining the amount of iodine ($I_2$) being injected into the laser or resonant cavity. Knowledge of the iodine mass flow rate is essential in an understanding of the operation of such a chemical laser. This is because the excited oxygen/iodine ratio is extremely critical in the operation of the laser, in that either too little or too much iodine will cause the efficiency of the laser to drop drastically.

The present method of injection of iodine within the resonant cavity consists of passing an inert gas such as argon over a container of heated iodine (60° C.), thus entraining some unknown density of iodine therein. This mixture is then passed into a slit nozzle for subsequent mixing with excited oxygen.

There are well-established techniques for measuring the amount of excited oxygen entering the laser but there are no techniques capable of accurately measuring the mass flow rate of iodine. A measurement of the temperature of the iodine container does not give a reliable iodine density reading because of the nonequilibrium situation; i.e., a saturated vapor pressure above the iodine crystals is not achieved because of the rapid flow of the argon or inert gas carrier. Hence, one cannot even be certain that higher argon flow rates lead to higher iodine density being injected into the laser.

As pointed out hereinabove a determination of the mass flow rate of iodine is essential to proper chemical laser operation. More specifically, too much iodine will cause the so-called "$^1\Sigma$ catastrophe" where the kinetics of the oxygen-iodine system are altered to such an extent that the laser will not operate. Too little iodine causes the extractable power to drop. In addition, knowledge of the iodine mass flow rate greatly aids in the modeling of laser systems.

It is therefore readily apparent from the above recitation that an iodine mass flow rate detection system or, more generally, a halogen flow rate detection system is extremely desirable, and is of utmost importance in, for example, the utilization of chemical lasers.

SUMMARY OF THE INVENTION

The instant invention overcomes the problems set forth hereinabove by providing a simple and accurate diagnostic system for determining the mass flow rate of a halogen such as iodine and, in addition, can be readily coupled or incorporated into the iodine feedline of an iodine/oxygen chemical laser.

The halogen mass flow rate detection system of this invention utilizes an absorption cell through which an inert gas having entrained therein a halogen is passed. In addition, passing through the absorption cell is an electromagnetic beam of radiation at a preselected wavelength in the bound-continuum absorption region. This invention utilizes molecular absorption for determining the concentration of the halogen.

The technique of this invention utilizes absorption of the halogen on a bound-continuum transition. By using the bound-continuum transition the absorption coefficient is essentially constant. Thus, the measured absorbance varies linearly with the number density of the absorber. This measurement is also extremely insensitive to temperature and added bath gas pressure which would ordinarily prevent severe complications in the bound-bound absorption transition. Consequently, the system of this invention is insensitive to carrier gas pressure and temperature which are varied in actual chemical laser operation.

It is therefore an object of this invention to provide a detection system which is capable of simply and accurately measuring the mass flow rate of a halogen.

It is a further object of this invention to provide a method for simply and accurately measuring the mass flow rate of a halogen.

It is another object of this invention to provide a detection system for measuring the mass flow rate of a halogen such as iodine and which can be readily incorporated within a chemical laser system.

It is still another object of this invention to provide a halogen mass flow rate detection system which is insensitive to temperature and gas pressure.

It is still another object of this invention to provide a halogen mass flow rate detection system in which absorption measurements are made on a bound-continuum transistion.

It is still a further object of this invention to provide a halogen mass flow rate detection system which is economical to produce and which utilizes conventional, currently available components that lend themselves to standard, mass producing manufacturing techniques.

For a better understanding of the present invention, together with other and further objects thereof, reference is made to the following description taken in conjunction with the accompanying drawing and its scope will be pointed out in the appended claims.

DETAILED DESCRIPTION OF THE DRAWING

FIG. 3 is a schematic representation, shown partly in cross section, of the halogen mass flow rate detection system of this invention incorporated within a chemical laser.

DETAILED DESCRIPTION OF THE PREFERRED EMBODIMENT AND METHOD

Figure 1:
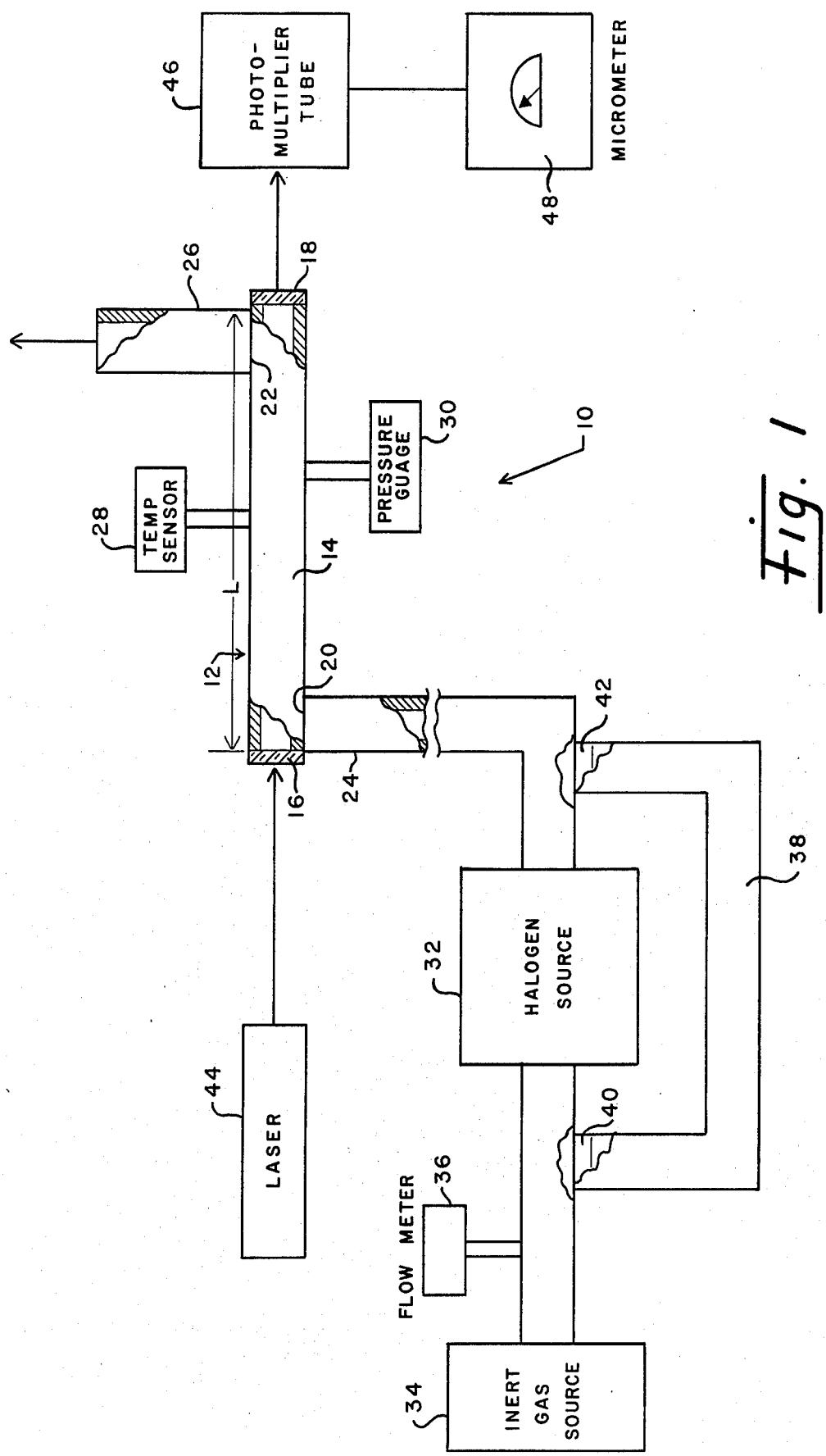
FIG. 1 is a schematic representation, shown partly in cross section, of the halogen mass flow rate detection system of this invention.

Reference is now made to FIG. 1 of the drawing which shows in detail the halogen mass flow rate detection system 10 of this invention. Detection system 10 includes therein an absorption cell 12 made up of an elongated cylindrically-shaped tube 14 of predetermined length, L, and which has optically transparent windows 16 and 18 enclosing the ends thereof. Also, situated adjacent each end are entrance and exit ports 20 and 22, respectively, with the diameter of each of the ports being substantially equal to the internal diameter of elongated tube 14 of absorbtion cell 12. Connected to entrance port 20 is an inlet line 24 while connected to exit port 22 is an exit line 26 which enables a halogen entrained inert gas to pass therethrough. In addition, operably connected to tube 14 is any suitable temperature sensor 28 in the form of, for example, a conventional thermocouple, and any suitable conventional pressure gauge 30.

Reference is now made specifically to the inlet end of absorption cell 12. Situated within inlet line 24, although its specific location therein is not essential, is any conventional halogen source which may, for example, in this invention be in the form of a container 32 for holding iodine crystals therein. At the furthest end of inlet line 24 from absorption cell 12 is an inert gas source 34 in the form of, for example, argon. Any suitable, conventional flow meter 36 is interconnected within line 24 juxtaposed inert gas source 34 in order to determine the mass flow rate of the inert gas (argon) as it passes through the halogen (iodine) on its way to the absorption cell 12.

In addition, a by-pass line 38 is interposed within inlet line 24 so as to provide a path for the inert gas to circumvent the halogen container 32 when necessary during the procedure of halogen mass flow rate detection as described in detail hereinbelow during the operation of the detection system 10 of this invention. Conventional valves 40 and 42 are located within by-pass line 38 so as to enable the inert gas to pass directly to the halogen container 32 or by-pass the halogen container 32, if desired.

It should be noted, however, that although a by-pass line 38 is shown as a means of preventing the passage of the inert gas through the halogen, any other arrangement which would prevent the entrainment of the halogen by the inert gas under selected conditions would also be acceptable with this invention. For example, it would be possible to freeze the halogen crystals in container 32 and thereby prevent their entrainment.

Optically aligned with one of the end windows 16 of absorption cell 12 is any suitable, conventional laser 44 (such as an argon laser 44) which is capable of passing a beam of electromagnetic radiation at a preselected wavelength through absorbtion cell 12. Receiving the electromagnetic radiation passing through cell 12 and positioned juxtaposed and in optical alignment with the other window 18 of absorption cell 12 is an intensity detector 46 in the form of, for example, a conventional photomultiplier tube such as an RCA 4832 PMT. Electrically connected to photomultiplier tube 46 is any suitable current flow recording or registering means 48 such as a conventional microammeter. Microammeter 48 is capable of registering the current flow produced by the change of intensity detected by photomultiplier tube 46.

It is essential for an understanding of the technique of mass flow rate detection of this invention set forth in detail hereinbelow to first understand the principal of optical absorption of radiation. Therefore, the following analysis is presented in abbreviated format.

Optical absorption of radiation from some ground state to an excited state by an ensemble of absorbing molecules is usually defined by some form of Beer's Law:

$$I_\nu(T) = I_\nu(o) e^{-N\sigma_\nu L} \quad (1)$$

where

I(T)≡intensity of probe after a single pass through the medium
I(o)≡initial intensity of probe beam
N≡number density of absorbtion molecules
$\sigma_\nu$≡absorbtion cross section
L≡cell length
ν≡optical frequency of probe beam.

This seemingly simple description of absorption is actually experimentally very complicated because the actual absorption measured depends upon the line shapes of both the absorber and probe. Consequently, the measured absorption is strongly influenced by experimental conditions.

Figure 2:
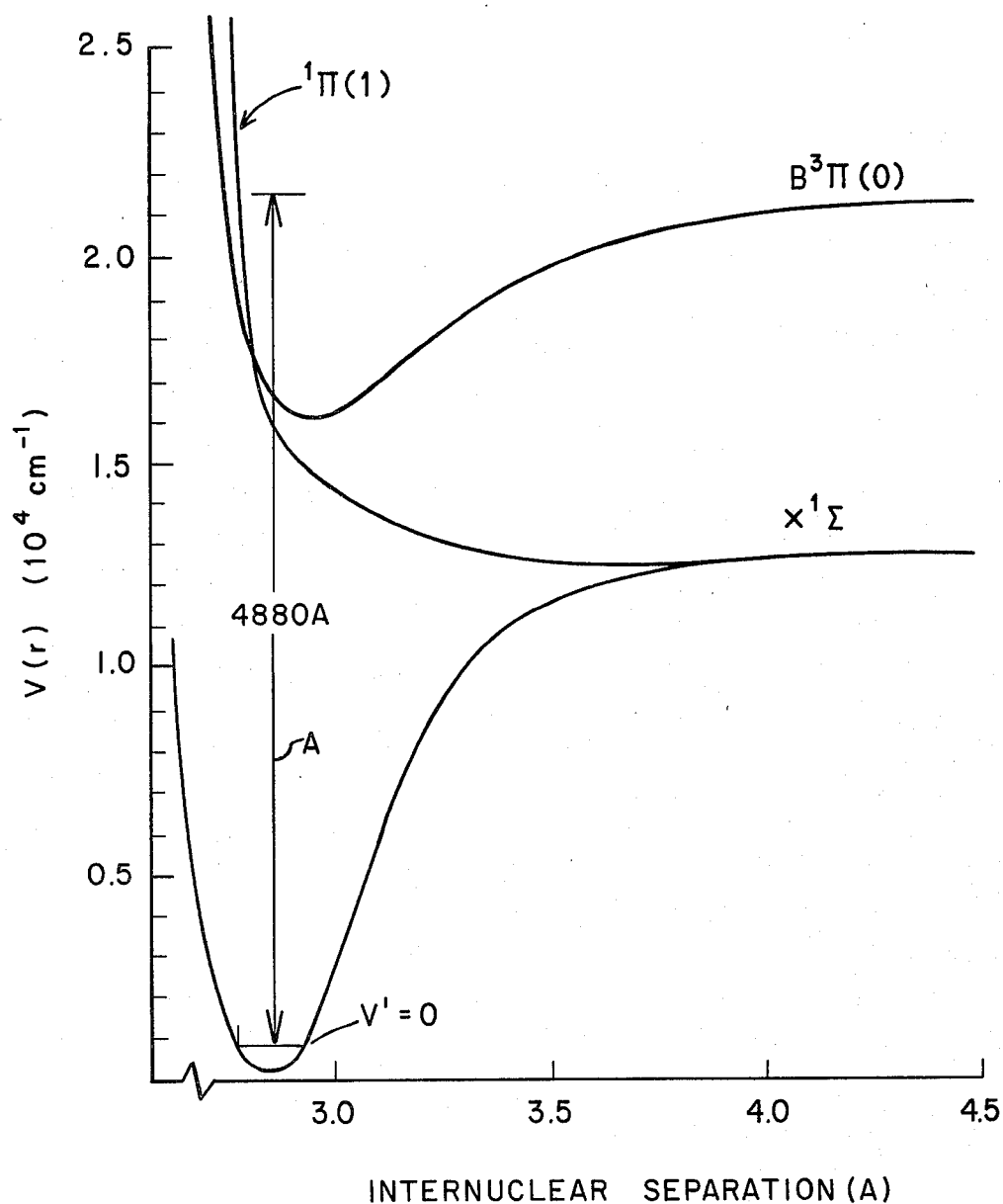
FIG. 2 is a graph representative of the potential curves for iodine visible transitions utilized in the technique of measuring mass flow rate of this invention.

The situation is greatly simplified if the absorption is from a stable ground state to a continuum of states. This can be illustrated with the aid of FIG. 2. FIG. 2 shows that the potential curves of the ground state $X^1\Sigma$ and the excited $B^3\pi(o)$ state dissociation energy is 20020 cm$^{-1}$. This means that photons of wavelengths shorter than 4995 A will, when absorbed by $I_2$, dissociate the molecule into two iodine atoms. For wavelengths longer than 4995 A, the absorption is between discrete levels and the absorption cross section depends upon both excited state and ground state wave functions. This situation is extremely simple in the bound-continuum absorption transition. Therefore, the instant invention relies upon the bound-continuum absorption transition illustrated by the arrow, A, in FIG. 2. The terminal level is in the continuum region since it lies above the dissociation energy. It can be shown that the absorption coefficient k for this case is given by the following equation:

$$k_\nu = \frac{8\pi\nu}{3hc} \frac{N}{q_\nu} \frac{g_A}{g_B} |RE|^2 \frac{dr}{d\nu} \sum_{\nu''} \psi^2_{\nu''}(r) e^{-E\nu''/kT} \quad (2)$$

For the sake of brevity the constants of the above equation are not defined herein but should be recognized by one skilled in the art and can be found in Herzberg, G., *Spectra of Diatomic Molecules*, Van Nostrand Reinhold Co., New York, NY, (1965) if desired. The important points to remember, however, are that the absorption coefficient at a given frequency depends upon the number density of ground state absorbers, N, and upon the vibrational probability distribution of the ground state set forth below:

$$\sum_{\nu''} \psi^2_{\nu''}(r) e^{-E\nu''/kT} \quad (3)$$

The term (dr/dν) is the gradient of the excited state potential curve evaluated at internuclear separation r, fixed by the absorption frequency ν. The fact that the absorption coefficient depends only upon the vibrational distribution of the ground state makes absorption measurements fairly insensitive to the temperature of the absorbing molecules and buffer gas pressure in the cell.

Reference is once again made to FIG. 1 of the drawing which illustrates the absorption cell 12 of the halogen flow rate detection system 10. Absorption cell 12 is made of a known length, L. This is accomplished by placing the entrance and exit ports 20 and 22 near the ends of the elongated tube 14 of cell 12. By making the diameter of entrance and exit ports 20 and 22 substantially the same as the diameter of the cell 12 any gas dynamic effect of any suitable halogen such as iodine which flows through the cell is minimized.

In the case of the mass flow rate detection system 10 of this invention shown in FIG. 1 of the drawing the probe source utilized therewith is a low power argon-ion laser 44. An example of the operative power for laser 44 may be only a milliwatt of power at a preselected wavelength of, for example, 4880 A although substantially less power may actually be required. The length, L, of absorption cell 12 can be varied to account for different halogens or iodine concentrations, however, for nominal conditions a length, L, for tube 14 of only 5 through 10 centimeters is ample. For lower concentrations, such an in kinetic studies, a larger tubular length can be used with this invention.

Since it is essential for the technique of this invention to establish a number density, N, for the iodine in cell 12, it is necessary to measure the absorbance of the 4880 A laser line, that is, at the bound-continuum absorption region. The absorbance, A, is related to the number density, N, by the following formula:

$$A = N\sigma L$$

where N = number density of the molecular iodine; $\sigma$ = absorption cross section at the preselected wavelength of 4800 A = $1.6 \times 10^{-18}$ cm$^2$; and L = absorption cell length.

The above relationship has been found to be an accurate description of the absorption from 0-10 Torr of iodine and from 0-20 Torr of buffer gas (Ne). To determine the iodine mass flow rate out of exit line 26 as depicted in FIG. 1 of the drawing it is also necessary to know the amount of inert gas such as argon in which the halogen such as iodine is entrained. The iodine is carried into the absorption cell 12 and from cell 12 into the resonant cavity of a chemical laser (for example) by the inert gas (argon) which passes over the halogen (iodine) in container 32.

In setting forth the steps of the method of this invention for rapidly, accurately and reliably determining the mass flow rate of a halogen such as iodine entrained in an inert gas such as argon it is first necessary to pass only the inert gas (argon) at a preselected mass flow rate, $\dot{m}_{IG}$, determined by flow meter 36 through the absorption cell 12 of a preselected tubular length, L. The temperature, T, in cell 12 is detected by temperature sensor 28.

At the same time a determination is made of the pressure, $P_{IG}$, of the inert gas by pressure gauge 30 within the absorption cell 12. Thereafter, a beam of electromagnetic radiation from laser 44 at a predetermined wavelength (i.e., at the bound-continuum absorption line) of, for example, 4880 A and of a predetermined power of, for example, a milliwatt is passed through absorption cell 12 while only the inert gas (argon) flows therethrough. This is accomplished by circumventing the iodine or halogen source in container 32 by means of by-pass line 38. A measurement of the intensity, $I_o$, of the beam after being passed through cell 12 is detected by photomultiplier tube 46 and registered by microammeter 48.

Thereafter, the inert gas (argon) at the same preselected mass flow rate, $\dot{m}_{IG}$, is passed through the halogen (iodine) in container 32 in order to entrain the halogen therein. The halogen entrained inert gas thereafter passes through absorption cell 12. The same electromagnetic beam of radiation from laser 44 is again passed through absorption cell 12, however, at this time the halogen entrained inert gas is also passing through absorption cell 12. Measurement is now made of the intensity, $I_t$, of the beam after being passed through the halogen entrained inert gas. The absorbance, A, of the halogen is now determined by the following equation $A = \ln(I_o/I_t)$.

The number density, $N_H$, of the halogen (iodine) is determined by the equation $N_H = A/\sigma L$ where $\sigma$ is defined as absorption cross section of the inert gas at the predetermined wavelength 4880 A referred to hereinabove and which is published as $1.6 \times 10^{-18}$ cm$^2$. A determination of the mass flow rate, $\dot{m}_H$, of the halogen which, for example, may preferably be iodine, can be determined by the following equation $\dot{m}_H = \dot{m}_{IG}(N_H/N_{IG})$ wherein $N_{IG}$ is the number density of the inert gas which, for example, may preferably be argon. The number density of the inert gas, $N_{IG}$, can be determined by the equation $(P/760)(270°\text{ K.}/T)(2.68 \times 10^{19})$ in which P is the pressure of the inert gas within cell 12.

Although the halogen mass flow rate detection system 10 of this invention is operable in and by itself it is extremely effective in measuring the mass flow rate of, for example, iodine within an iodine/oxygen chemical laser. Therefore, reference is now made to FIG. 3 of the drawing which shows in detail the incorporation of halogen mass flow rate detection system 10 of this invention within a chemical laser system 60. Chemical laser system 60 without the incorporation of halogen mass flow rate detection system 10 of this invention therein is conventional in its makeup and is of the type found in the publication by W. E. McDermott et al entitled "An Electronic Transistion Chemical Laser", Applied Physics Letters, 32 (8), Apr. 15, 1978.

Since the chemical laser system 60 is of conventional design only the elements necessary for use with halogen mass flow rate detection system 10 will be described and have numerals associated therewith as illustrated in FIG. 3 of the drawing. Consequently, the remaining elements of chemical laser system 60 will not be found in FIG. 3 of the drawing since the operation of chemical laser system 60 is conventional and well within the purview of one having ordinary skill in the art.

More specifically, and still referring to FIG. 3 of the drawing, the laser cavity or resonant cavity 62 is illustrated as an elongated tubular element having reflective surfaces 61 and 63 at opposite ends thereof. An injection tube 64 is shown entering resonant cavity 62. The injection tube 64 allows for a passage therethrough of the iodine/argon mixture and excited oxygen as shown in the drawing. The excited oxygen enters through inlet 66 while the iodine in its crystalline form is found in an iodine container 68. Any suitable inert gas such as argon emanating from argon source 70 is passed through a heater 80 before passing through the crystal iodine found in container 68. The argon entrains the iodine therein for subsequent passage through absorption cell 12 before combining with the excited oxygen.

The halogen or iodine mass flow rate detection system 10 of this invention is interposed within the laser system 60 between the inlet line 66 of the excited oxygen and the inlet line 82 of the iodine/argon mixture. The remaining elements of the halogen (iodine) mass flow rate detection system 10 are identical to the elements shown in FIG. 1 of the drawing with like references numerals being utilized in both FIGS. 1 and 2 for identical elements.

The operation of the halogen (iodine) mass flow rate detection system 10 utilized with chemical laser system 60 is identical to the operation of halogen mass flow rate detection system 10 described in detail hereinabove and therefore need not be repeated. Thus, the density of the iodine within the chemical laser 60 can be monitored as the argon carrier flow is varied. By knowing the mass flow rate and pressure of argon, the mass flow rate of the iodine entering resonant cavity 62 can be easily and accurately determined by the formulae presented hereinabove with respect to the operation of halogen mass flow rate detector 10.

Although this invention has been described with reference to a particular embodiment and methods, it will be understood to those skilled in the art that this invention is also capable of further and other embodiments within the spirit and scope of the appended claims.

We claim:

1. A halogen mass flow rate detection system comprising an absorption cell, means connected to said absorption cell for passing either an inert gas or a halogen entrained inert gas thereinto, means connected to said absorption cell for passing either said inert gas or said halogen entrained inert gas out of said absorption cell, means adjacent one end of said absorption cell for providing a beam of electromagnetic radiation at a predetermined wavelength and for passing said beam of radiation through said absorption cell, said wavelength being in the bound-continuum region and said radiation being at a predetermined power, means adjacent the other end of said absorption cell for receiving said beam of electromagnetic radiation passing through said absorption cell and for detecting the intensity thereof, and means operably connected to said absorption cell for measuring the pressure of said inert gas passing therethrough, whereby a relationship between the detected intensity of said electromagnetic beam of radiation passing through only said inert gas and the detected intensity of said electromagnetic beam of radiation passing through said halogen entrained inert gas can be established, so as to then determine said halogen mass flow rate.

2. A halogen mass flow rate detection system as defined in claim 1 further comprising means connected to said absorption cell for measuring the temperature within said absorption cell.

3. A halogen mass flow rate detection system as defined in claim 2 wherein said absorption cell comprises an elongated tube having an internal diameter of a preselected size and said inert gas or halogen entrained inert gas passing means comprises a hollow member having an internal diameter which is substantially the same as said preselected size.

4. A halogen mass flow rate detection system as defined in claim 3 and further comprising an inert gas source connected to one end of said inert gas or halogen entrained inert gas passing means, and the other end thereof being connected to said absorption cell.

5. A halogen mass flow rate detection system as defined in claim 4 and further comprising a halogen source connected to and intermediate the ends of said inert gas or halogen entrained inert gas passing means.

6. A halogen mass flow rate detection system as defined in claim 5 wherein said inert gas or halogen entrained inert gas passing means further comprises means for selectively circumventing said halogen source.

7. A halogen mass flow rate detection system as defined in claim 6 wherein said means for selectively circumventing said halogen source comprises a bypass line having a pair of valves therein.

8. A halogen mass flow rate detection system as defined in claim 7, and further comprising means connected to said intensity detecting means for registering said intensity of said electromagnetic beam passing through said absorption cell.

9. A halogen mass flow rate detection system as defined in claim 8 wherein said electromagnetic beam providing means comprises a laser.

10. A method of rapidly, accurately and reliably determining the mass flow rate of a halogen which is entrained in inert gas comprising the steps of:
 (a) passing an inert gas at a preselected mass flow rate, $\dot{m}_{IG}$, through an absorption cell of preselected length, L, and at a preselected temperature, T;
 (b) determining the pressure, $P_{IG}$ of said inert gas within said absorption cell;
 (c) passing a beam of electromagnetic radiation of predetermined wavelength in the bound-continuum region and at a predetermined power through said absorption cell while only said inert gas flows therethrough;
 (d) detecting the intensity, $I_o$, of said beam after being passed through only said inert gas in said absorption cell;
 (e) passing said inert gas at said preselected mass flow rate through a halogen in order to entrain said halogen therein;
 (f) passing said halogen entrained inert gas through said absorption cell;
 (g) passing said beam of electromagnetic radiation through said absorption cell while said halogen entrained inert gas flows therethrough;
 (h) detecting the intensity, $I_T$, of said beam after being passed through said halogen entrained inert gas;
 (i) determining the absorbance, A, of said halogen by the equation $A = \ln(I_o/I_t)$;
 (j) determining the number density, $N_H$, of said halogen by the equation $N_H = A/\sigma L$ where $\sigma$ is defined as the absorption cross section of said inert gas at said predetermined wavelength; and
 (k) determining said mass flow rate, $\dot{m}_H$, of said halogen by the following equation: $\dot{m}_H = \dot{m}_{IG}(N_H/N_{IG})$ wherein $N_{IG}$ = number density of said inert gas = $(P_{IG}/760)(270° K./T)(2.68 \times 10^{19})$.

* * * * *